United States Patent [19]

Yannas et al.

[11] 4,448,718

[45] May 15, 1984

[54] METHOD FOR THE PREPARATION OF COLLAGEN-GLYCOSAMINOGLYCAN COMPOSITE MATERIALS

[75] Inventors: Ioannis V. Yannas, Newton; James F. Kirk, Cambridge, both of Mass.

[73] Assignee: Massachusetts Institute of Technology, Cambridge, Mass.

[21] Appl. No.: 531,804

[22] Filed: Sep. 13, 1983

[51] Int. Cl.$^3$ ............... C07G 7/00; C08H 1/00; C08H 1/06
[52] U.S. Cl. ............... 260/123.7; 106/155; 106/157; 128/335.5; 128/DIG. 8
[58] Field of Search ............... 260/123.7; 106/155, 106/157

[56] References Cited

U.S. PATENT DOCUMENTS

| 4,060,081 | 11/1977 | Yannas et al. | 128/156 |
| 4,233,360 | 11/1980 | Luck et al. | 260/123.7 X |
| 4,280,954 | 7/1981 | Yannas et al. | 260/123.7 |
| 4,350,629 | 9/1982 | Yannas et al. | 260/123.7 |
| 4,416,814 | 11/1983 | Battista | 260/123.7 X |

OTHER PUBLICATIONS

Ruderman et al., J. Biomed. Mater. Res. 7, 263-265, (1973).

*Primary Examiner*—Howard E. Schain
*Attorney, Agent, or Firm*—Arthur A. Smith, Jr.; Thomas J. Engellenner; Richard Neeley

[57] ABSTRACT

A process for preparing a crosslinked collagen-glycosaminoglycan composite material which comprises forming an uncrosslinked composite material from collagen and a glycosaminoglycan and contacting the uncrosslinked composite with a gaseous aldehyde until a crosslinked product having an $M_c$ of from about 800 to about 60,000 is disclosed along with composite materials prepared by this process. Artificial skin produced by this process is more stable toward long-term storage than similar materials prepared using other methods of crosslinking.

10 Claims, No Drawings

METHOD FOR THE PREPARATION OF COLLAGEN-GLYCOSAMINOGLYCAN COMPOSITE MATERIALS

The invention described herein was supported in whole or in part by a grant from the National Institutes of Health.

BACKGROUND OF THE INVENTION

1. Field of the Invention

The present invention relates to a method for the preparation of biocompatible collagen-glycosaminoglycan composite materials by vapor phase crosslinking with aldehydes.

2. Description of the Prior Art

Composite materials made of collagen and glycosaminoglycan (GAG) have been shown to be highly useful for certain biochemical applications. For example, U.S. Pat. No. 4,060,081 (Yannas et al, 1977), the teachings of which are hereby incorporated by reference, discloses a multilayer membrane suitable for use as synthetic skin. The bottom layer, which is placed in contact with a woundbed, is a highly porous lattice comprising collagen that is crosslinked with GAG. This lattice provides a biophysical supporting structure in which cells can migrate and proliferate to heal the wound.

The typical procedures that have been used in the past to prepare collagen/GAG composite materials are described in U.S. application Ser. No. 30,183, filed on Apr. 16, 1979, now U.S. Pat. No. 4,280,954 and U.S. application Ser. No. 169,897, filed July 17, 1980, now abandoned; the teachings of both of these applications are herein incorporated by reference. Briefly, a preferred embodiment of these procedures comprises the following steps, in sequence:

1. Mechanically cutting and grinding a source of collagen into particulate form.
2. Soaking the particulate collagen in dilute acetic acid.
3. Homogenizing the solution in a blender.
4. Adding a source of glycosaminoglycan which has been ground into particulate form. Typically, enough GAG is added to the solution to comprise about 6% to about 12% by dry weight of the composite material. The collagen/GAG mixture normally co-precipitates out of the acidic solution and forms a fibrous dispersion.
5. Homogenizing the precipitate in a blender.
6. Freezing the solution quickly in a shallow pan.
7. Subjecting the frozen dispersion to a high degree of vacuum, thereby causing the acidic fluid to evaporate while the spatial configuration of the partially crosslinked fibrils is maintained.
8. Contacting the freeze-dried product with a solution containing a crosslinking agent such as glutaraldehyde.

The composite material thus formed may be treated by additional procedures to remove all traces of aldehyde and to increase the crosslinking density and strength of the composite material.

Furthermore, U.S. Pat. No. 4,350,629 to Yannas et al discloses a method for improving the biocompatibility of the composite materials made by this general method. An aqueous dispersion of collagen is swollen in acid and contacted with a crosslinking agent prior to adding GAG to the solution. The resulting composite material causes extremely low or undetectable levels of blood platelet aggregation. The teachings of U.S. Pat. No. 4,350,629 are also hereby incorporated by reference.

Although the composite materials produced by the methods described in these patents and patent applications are extremely useful as synthetic skin and other prosthetic devices, certain problems still remain relating to storage and shelf-life of these materials.

In the current process for crosslinking porous sheets based on collagen and GAG, the sheets are placed in an aqueous solution of glutaraldehyde or a similar crosslinking agent. The crosslinked sheets are then rinsed in water and typically stored in an alcohol/water solution until ready for use as grafts. Storage in an alcohol/water solution has two disadvantages. First, the shelf-life of the collagen-GAG sheets in alcohol/water is limited to several weeks due to gradual degradation of collagen in the medium. Second, storage in a liquid makes transporation of the artificial skin cumbersome.

Both of these problems could be resolved if the collagen-GAG sheets could be crosslinked and stored in a dry state. Such an alternative procedure would allow storage of the sheets in the dry state with attendant increased shelf-life and significantly increase convenience in transporation. Unfortunately, freeze drying of the porous sheets following wet processing leads to significant loss in the porosity of the sheets and in substantial or total loss of performance of the sheets as grafts for the treatment of wounds. A different treatment is therefore needed for the production of artificial skin. Ruderman et al, *J. Biomed. Mater. Res.*, 7, 263–265 (1973), discloses a vapor-phase crosslinking of collagen sponges with formaldehyde. However, the tensile strength of the untreated sponge was approximately 5 times greater than the tensile strength of the treated sponges; i.e., the bonds formed by the reaction with formaldehyde were said to be weaker than the hydrogen bonds they replaced. Accordingly, this reference teaches against the use of vapor-phase treatment with aldehydes to produce crosslinking in synthetic skins since the strength of a synthetic skin is very important.

Accordingly, there remained prior to this invention a need for new methods for crosslinking collagen-GAG composite materials intended for use as artificial skin.

SUMMARY OF THE INVENTION

Accordingly, it is an object of this invention to provide a process for preparing a crosslinked collagen-glycosaminoglycan composite material which provides a crosslinked material capable of long-term storage.

This and other objects of the invention as will hereinafter become more readily apparent have been accomplished by providing a process for preparing a crosslinked collagen-glycosaminoglycan composite material, which comprises:

forming an uncrosslinked composite material from collagen and a glycosaminoglycan; and contacting said uncrosslinked composite with a gaseous aldehyde until a crosslinked product having an $M_c$ of from about 800 to about 60,000 is formed.

DESCRIPTION OF THE PREFERRED EMBODIMENTS

The present invention arose with the discovery that collagen-glycosaminoglycan composite materials could be crosslinked using gaseous aldehydes to produce a crosslinked product suitable for use as an artificial skin. Previously, the prior art had indicated that if a gaseous aldehyde, such as formaldehyde vapor, was used to crosslink collagen, the product formed would have a tensile strength less than one-fifth that of the original collagen material. Surprisingly, the inventors have discovered that a collagen-glycosaminoglycan composite material can be crosslinked with a gaseous aldehyde to produce an artificial skin which is suitable for clinical applications.

The present invention contemplates crosslinking collagen and glycosaminoglycan materials by forming an uncrosslinked composite material made from collagen and a glycosaminoglycan and exposing this uncrosslinked material to a gaseous aldehyde until a crosslinked product having an $M_c$ of from about 800 to about 60,000 is formed. $M_c$ is the average molecular weight of the segments between adjacent crosslinks.

Methods for forming the uncrosslinked composite are described in full in the patents and patent applications previously cited and incorporated by reference. Generally, forming the composite material involves preparing separate solutions of a collagen and a glycosaminoglycan source. A collagen dispersion may be formed, for example, by contacting finely divided hide or another source of collagen with an aqueous solution of acid. The collagen is purified by repeated precipitation from a turbid dispersion in a buffered solution, for example 0.05 M acetic acid and 0.2 M sodium dihydrogen diphosphate. After purification, the resulting collagen dispersion may be stored at 4° C. until further processing is required. A glycosaminoglycan (mucopolysaccharide) solution can be prepared from any source of a glycosaminoglycan, for example sodium heparin, hyaluronic acid or chondroitin 6-sulfate. Sodium heparin may be obtained from hog intestinal mucosa, hyaluronic acid may be obtained from rooster combs, and chondroitin 6-sulfate may be obtained from shark cartilage by known methods. The glycosaminoglycan is dissolved in, for example, a citric acid-phosphate buffer at, for example, 1% w/v and stored at 4° C. until further needed.

One method of forming an uncrosslinked composite material is to coprecipitate collagen with a glycosaminoglycan. One suitable method for conducting this coprecipitation is to thoroughly agitate a dilute collagen dispersion and to add a dilute solution of a glycosaminoglycan dropwise to the collagen dispersion. The addition of the glycosaminoglycan causes collagen to coprecipitate forming a tangled mass of collagen fibrils coated with the glycosaminoglycan. When sufficient material has precipitated, the fibrils can be separated from the solution by filtration, formed into the desired shape, and dried. More complete descriptions of the formation of the uncrosslinked composite materials is found in the previously cited patents and patent applications.

Since as previously indicated the present method is intended to increase storage life and dryness of the composite material is therefore important, the uncrosslinked material should be dried to the greatest extent practical. Some precaution which must be observed in the early stages of drying since drying wet collagen at greater than 40° C. causes denaturation into gelatin. Thus, the composite should be dried at a lower temperature than 40° C. until the water content reaches a low level, for example, about 1% water by weight. Afterwards, higher temperatures may be used to remove residual water, if desired. For example, partially dried sheets formed of the composite material may be dried in a vacuum oven at, for example, 105° C. overnight. The resulting dried material preferably contains less than 1.0% by weight water and more preferably less than 0.2% water. Although higher percentages of water will not prevent the crosslinking reaction from taking place, dry materials are preferred for storage purposes as previously indicated. Vacuum drying of the composite material while heating is sometimes referred to in this application as a "dehydrothermal" processing step.

The uncrosslinked composite material is then exposed to a gaseous aldehyde until a crosslinked product having an $M_c$ of from about 800 to about 60,000, preferably from about 8,000 to about 25,000, and most preferably about 12,000, is formed. By gaseous aldehyde is meant not only those aldehydes which exist in the physical state of a gas at normal temperature and pressure (25° C., 1 atmosphere) but also vapors produced from aldehydes which are liquids or even solids under the conditions used during the crosslinking step. Liquids and solids can be used under any condition which do not harm the uncrosslinked composite material and produce appreciable vapor pressure for the aldehyde. Preferred are aldehydes having a boiling point of less than 200° C. Especially preferred are aliphatic and aromatic (e.g., phenyl) mono- and dialdehydes having 1 to 8 carbon atoms. Examples of suitable compounds include methanal (formaldehyde), ethanal (acetaldehyde), propanal, 2-methylpropanal, butanal, pentanal, hexanal, heptanal, octanal, ethanedial (glyoxal), propanedial, butanedial, pentanedial (glutaraldehyde), benzaldehyde, and o-tolualdehyde. Preferred aldehydes, because of their ready availability, are formaldehyde, acetaldehyde, glyoxal, and glutaraldehyde. Of these, glutaraldehyde is most preferred.

A dry, uncrosslinked composite material is contacted with a gaseous aldehyde at a temperature of from 4° C. to 150° C., preferably from 20° C. to about 100° C., and most preferably at about 25° C., until a crosslinked product having an $M_c$ of from about 800 to about 60,000 is formed. It is particularly preferred to select conditions based on the physical properties of the aldehyde being used which produce a vapor concentration of 0.5–1.0% aldehyde in an atmosphere otherwise consisting of air (which may also contain water vapor) at a pressure of one standard atmosphere. If produced by exposing the composite material to vapors from an aqueous solution of an aldehyde, at least 4 mole % of the solution vapor is preferrably aldehyde. The amount of exposure time will vary as is well understood to those skilled in the art with the temperature and the concentration of the gaseous aldehyde (aldehyde vapor). If the amount of time for a particular set of conditions is not known, it can be determined by the following simple experiment. Separate strips from a collagen-GAG sheet are contacted with a gaseous aldehyde under the conditions for which a contacting time is desired to be known. Strips are removed at various time intervals and $M_c$ is determined using well known procedures. For example, $M_c$ can be determined by measuring the stress-strain behavior of the crosslinked composites. This technique is described in Treloar, *The Physics of Rubber Elasticity*, 2nd Edition, Clarendon Press, 1958; the technique as described in this reference is herein incorporated by reference. Generally, this technique consists of the following steps:

(1) Strips of rehydrated collagen/GAG composite material are denatured in a 0.9% saline solution at 80° C. for 5 minutes prior to testing.

(2) One strip at a time is mounted in Istron test grips, and the sample is reimmersed in 0.9% saline at 80° C.

(3) The strip is elongated to 1.05, 1.10, and 1.15 times its original length (waiting 4-5 minutes between elongation steps). The load at the end of each elongation is recorded.

(4) After the last elongation, the strip is returned to the gage length. Its width and thickness are measured along with the wet weight of the gage portion of the strip.

(5) The gage portion is dried at 105° C. overnight, and its dry weight is taken.

(6) The stress at each elongation (in pounds per square inch) is calculated using the width, thickness, and load. The stress is plotted vs. elongation, and the slope (m) is found.

$$m = \frac{stress_i}{(\alpha_i - 1/\alpha_i^2)}, \text{ where } \alpha_i = \frac{test\ length_i}{gage\ length_i}$$

(7) The volume fraction is calculated using the following formula:

$$V_2 = \frac{dry\ weight}{(1.3)(wet\ weight) + dry\ weight}$$

(8) The mass between crosslinks is then calculated using the following formula:

$$M_c = [(5.535 \times 10^5)(V_2)^{\frac{1}{3}}/m]$$

Once time intervals are determined which produce the desired $M_c$, future strips or sheets of the same thickness can be produced under the same conditions merely by controlling the exposure (contact) time.

Because collagen/GAG composite materials are highly porous and gaseous aldehydes diffuse freely through the pores, this method of crosslinking is suitable without regard to the thickness of the sample being crosslinked. For example, collagen/GAG composite material generally has a porosity in the range of from 50μ to 500μ, with an average pore diameter of about 200μ. Accordingly, crosslinking of material having a thickness of up to ¼ inch (6 mm) or even higher is easily attained. However, this method is particularly suited to crosslinking the thin sheets of collagen/GAG prepared for use as artificial skin. Such sheets generally have a thickness of about 90/1000 of an inch (about 2 mm).

In a preferred embodiment of the invention, preformed, uncrosslinked composite material is enclosed within a chamber which additionally contains air and a gaseous aldehyde. The gaseous aldehyde may be introduced by passing the aldehyde in the form of a gas or vapor into the chamber from an outside source or by merely placing an open container of the aldehyde or a solution of the aldehyde in water or an organic solvent (such as methanol) into the closed chamber. After a suitable period of time, determined as described above, the crosslinked product is removed from the chamber.

In one preferred embodiment of the invention, preformed, uncrosslinked composite material is placed inside a closed chamber containing an aqueous solution of glutaraldehyde. After from 15 minutes to 50 hours, preferably from 30 minutes to 3 hours, the crosslinked product is removed from the chamber. Uncrosslinked strips undergo approximately 10% shrinkage in length when rehydrated prior to use. Strips which are exposed to glutaraldehyde vapor for less than 15 minutes also undergo shrinkage but to an extent which is less than for untreated samples. Strips contacted with glutaraldehyde vapor for more than 15 minutes do not show measurable shrinkage upon rehydration.

Variations on the procedures described herein that produce the same cross-linking effect are contemplated as being within the scope of the present invention. For example, the order of the dehydrothermal and vapor-cross-linking steps may be reversed. If dehydrothermal treatment follows vapor crosslinking, the dehydrothermal process boils off any free aldehyde that may still remain in the composite and also leaves the composite in a sterile state. This simplifies the manufacturing process and is a preferred embodiment of the invention.

The invention now being generally described, the same will be better understood by reference to certain specific examples which are included herein for purposes of illustration only and are not intended to be limiting of the invention or any embodiment thereof, unless specified.

EXAMPLE 1

Preparation of Collagen Dispersions and Mucopolysaccharide Solutions

Collagen was prepared by precutting limed calf hides into strips ⅜" wide and then into thin pieces. These thin pieces of hide were contacted with three part of water containing 0.3% propionic acid and 0.1% benzoic acid. Equilibrium was established after four hours at which time the solution had a pH approaching 5.3. The collagen slurry was separated from the water and ground to products of different particle sizes and structures with a centifugally acting cutter-grinder. The calf hide collagen slurry (1:1 water-to-hide weight ratio) had a gelatin content of about 2%. Additionally, it contained about 0.41% calcium and about 0.041% magnesium. Physically, the slurry was composed of highly entangled fibrillar aggregates.

The calf hide collagen slurry as purified by a repeated preipitation from a turbid dispersion in 0.05 M acetic acid with 0.2 M sodium dihydrogen diphosphate, $NaH_2PO_4$. After purification, collagen was dispersed in 0.05 M acetic acid or in a citric acid-buffer solution at pH 3.2 (0.1 M citric acid, 0.2 M sodium dihydrogen diphosphate). The dispersion was thoroughly homogenized in a Waring Blender until the absorbance at 440 millimicrons of a 0.3% (W/V) collagen dispersion was about 0.5 as measured on a spectrophotometer (Coleman Junior II A, Maywood, Illinois). The resulting collagen dispersions were stored at 4° C. until further processing was required.

Glycosaminoglycan (mucopolysaccharide) solutions were prepared from sodium heparin, hyaluronic acid and chondroitin 6-sulfate. Sodium heparin, from hog intestinal mucosa, 143 USP units of activity per milligram, was purchased from Abbott Laboratories, North Chicago, Illinois. Hyaluronic acid, from rooster comb was prepared by the method of Swann, D. A., *Biochem, Biophys. Acta,* 156, 17 (1968). The resulting hyaluronic acid contained 47.1% hexuronic acid and 42.6% hexosamine.

Chondroitin 4-sulfate from bovine nasal cartilage was prepared by the method described by Roden, L., Baker, J. R., Cifonelli, J. A. and Mathews, M. B., in *Methods of Enzymology,* V. Ginsburg, ed., vol. 28B, Academic Press, New York, p. 73. Heparan sulfate and dermatan sulfate were both extracted from hog mucosal tissues and purified by the methods described by Cifonelli, J. A. and Roden, L., *Biochemical Preparations*, 12, 12 (1968).

Chondroitin 6-sulfate, from shark cartilage-Grade B, was purchased from Calbiochem, San Diego, Calif. It contained 2.66% nitrogen, 37.2% glucuronic acid and 5.61% moisture.

Heparin, hyaluronic acid, chondroitin 4-sulfate, heparan sulfate, dermatan sulfate and chondroitin 6-sulfate were dissolved (1% W/V) in a citric acid-phosphate buffer pH 3.2. The mucopolysaccharide solutions were stored at 4° C.

EXAMPLE 2

Preparation of Collagen-Heparin and Collagen-Hyaluronic Acid Coprecipitates

Collagen 0.3% (W/V) dispersed in 0.05 M acetic acid was thoroughly agitated with a Telfon stirrer at 23° C. While the dispersion was mixing, heparin or hyaluronic acid 1% (W/V) in 0.05 M acetic acid was added dropwise from a buret at the rate of about 0.1 ml per second. The addition of mucopolysaccharide caused callagen to coprecipitate forming a tangeled mass of collagen fibrils coated with mucopolysaccharide which somewhat resembled a tangled ball of yarn. When 90% by weight of collagen was coprecipitated in this manner with 10% by weight mucopolysaccharide, a systematic mass balance showed that about 95% of the added mucopolysaccharide was coprecipitated.

After coprecipitation, the tangled mass of fibrils was homogenized in a Waring Blender until the fibrils were about 1 mm in length. The mixture of fibrils in 0.05 M acetic acid separated into two phases when left unagitated for more than five minutes, so that mixing was required before filtration. Filtration was performed by filtering the collagen-mucopolysaccharide dispersion under vacuum through a Buchner funnel containing Schleicher and Schuell (Keene, N.H.) filter paper No. 576. The coprecipitate was allowed to dehydrate under atmosperic conditions until the moisture content was about 20% by weight.

EXAMPLE 3

Preparation of Collagen-Chondroitin 6-Sulfate Coprecipitates

Collagen 0.3% (W/V) dispersed in a citric acid-phosphate buffer solution pH 3.2 at 23° C. was coprecipitated with a 1% (W/V) chondroitin 6-sulfate buffer solution pH 3.2 at 23° C. The coprecipitate was homogenized, filtered and allowed to dry in the atmosphere as described in Example 2.

In order to maintain high porosity in the product, as is often the case with synthetic skin, the composite was freeze dried at a temperature of −50° C. and a vacuum of 0.06 mm Hg. The product was then placed in a vacuum oven and exposed to a temperature of 105° C. and a vacuum of at least 0.3 mm Hg for 24 hours.

EXAMPLE 4

Crosslinking of Composite Materials

Composite materials prepared from coprecipitated collagen-GAG, prepared in a manner similar to that described above in Example 3, was formed into a thin sheet having a thickness of about 0.090 inch (2 mm) and dried in a vacuum oven overnight at 105° C. The dry sheet was cut into strips measuring 6.5 by 0.32 inch. The strips were attached end-to-end and placed on the ceramic shelf of a vented desiccator placed inside a fume hood maintained at 25° C. One-hundred milliliters of 25% aqueous glutaraldehyde solution (J. T. Baker Chemical Co., Phillipsburg, N.J.) was placed in the bottom of the desiccator. The strips were removed at regular intervals ranging from 5 minutes to 50 hours of exposure, and the average molecular weight between crosslinks ($M_c$) was determined for each strip using procedures described above. Measurement of $M_c$ were also made with strips which were not exposed to glutaraldehyde vapor but which were otherwise treated identically. Following treatment in the desiccator, all strips were rehydrated in 0.05 M acetic acid for at least 5 minutes, and any length change resulting from such immersion was noted prior to proceeding with measurements of $M_c$.

The measurements of the length change showed that strips which were untreated with glutaraldehyde vapor underwent approximately 10% shrinkage in length. Strips which were exposed to glutaraldehyde vapor over a period of 15 minutes or less also underwent shrinkage but to an extent which was significantly less than for untreated samples. Strips which were treated with glutaraldehyde vapor over more than 15 minutes did not show measurable shrinkage upon rehydration.

Measurements of $M_c$ showed that treated strips had a much lower average molecular weight between crosslinks (corresponding to a much higher density of crosslinks) than untreated strips. Whereas untreated strips showed $M_c$ values in excess of 100,000, strips which had been treated over a 2 hour period showed $M_c$ close to 50,000. The results of these measurements are shown in the following Table.

TABLE 1

| Exposure time (hrs) | Number of Samples | Mean $M_c$ ± Std Error of the Mean ($\times 10^3$) |
|---|---|---|
| Trial #1 - Long-term Exposure | | |
| 0 | 4 | 65.0 ± 13.0 |
| 1 | 3 | 12.8 ± 2.0 |
| 2 | 3 | 8.5 ± 1.7 |
| 4 | 3 | 7.7 ± 0.8 |
| 6 | 3 | 9.7 ± 0.9 |
| 8 | 2 | 12.8 ± 1.3 |
| 10 | 3 | 14.4 ± 4.0 |
| 20 | 3 | 8.7 ± 0.6 |
| 30 | 3 | 16.1 ± 2.3 |
| 40 | 3 | 8.6 ± 1.9 |
| 50 | 1 | 14.7 |
| Trial #2 - Short-term Exposure | | |
| 0 | 3 | 184 ± 33.2 |
| 5 | 3 | 104 ± 41.1 |
| 10 | 3 | 82.7 ± 5.4 |
| 15 | 3 | 58.3 ± 7.4 |
| 20 | 3 | 77.5 ± 15.1 |
| 30 | 3 | 50.2 ± 4.7 |
| 45 | 3 | 43.8 ± 8.3 |
| 60 | 3 | 40.4 ± 9.6 |

EXAMPLE 5

Tests to failure were run to determine the effect of the vapor crosslinking method on the ultimate tensile strength UTS, of collagen/glycosaminoglycan composites.

Four samples of #83007C foam were cut to measure 2.5 inches by 2.5 inches. Foam #83700C was a standard protocol form which had been processed up to and including the dehydro-thermal treatment.

Two of the samples were placed in a desiccator over 100 ml of glutaraldehyde, 25% w/w, for three hours. The other two samples were left untreated.

Tests to failure were run on dry samples and rehydrated, denatured samples. For both tests, a table model Instron with an "A" cell was used. The crosshead speed was two inches per minute and the gage length was one inch.

For the dry tests, five 0.5-inch by 2.5-inch specimens were cut from one sample each of treated and untreated foam. The specimens were placed in the test fixture and strained to failure.

For the "wet" tests, five 0.5-inch by 2.5-inch specimens were cut from one sample each of treated and untreated foam. These specimens were rehydrated for at least five minutes in 0.05 molar acetic acid. The specimens were then denatured for at least five minutes in 80° C., 0.9% saline solution.

After denaturing, the specimens were placed in the test fixture, submerged in 80° C., 0.9% saline and strained to failure.

The width of each specimen was measured to the nearest 32nd of an inch with a ruler after failure. The thickness was measured with a Mitutoyo pressure-sensitive micrometer to the nearest 1000th of an inch at the failure site.

The dry samples were weighed to the nearest milligram after the test. As the weights were all very nearly the same, the average of these weights was used for volume fraction calculations for the wet samples instead of drying and weighing those samples.

The nominal volume was calculated from the measurements taken by ruler and micrometer. The volume fraction, $V_2$, was calculated by equation 1:

$$V_2 = \frac{\text{specimen weight/nominal volume}}{\text{density of collagen (21.3 gr/in}^3\text{)}} \quad (1)$$

The stress at failure, UTS, was calculated by equation 2:

$$UTS = \frac{\text{failure load (grams)}}{453.6 \times \text{width} \times \text{thickness}} \quad (2)$$

The UTS for the collagen material itself is found by dividing the results of equation 2 by the volume fraction raised to the two-thirds power.

The mean tensile strengths for all four samples are given in Table 2 along with the adjusted UTS for the collagen material.

TABLE 2

| Sample # | Stress at Failure (PSI) | Mean UTS (± S.D.) | Mean $V_2$ | Adjusted UTS for collagen (PSI) |
|---|---|---|---|---|
| Dry, Untreated | | | | |
| 1-1 | 13.43 | | | |
| 1-2 | 15.68 | | | |
| 1-3 | 13.65 | 17.08 ± 5.82 | .025 | 199.8 |
| 1-4 | 15.31 | | | |
| 1-5 | 27.34 | | | |
| Dry, Treated | | | | |
| 2-1 | 20.46 | | | |
| 2-2 | 17.17 | | | |
| 2-3 | 9.52 | 12.55 ± 5.95 | .029 | 133.0 |
| 2-4 | 6.47 | | | |
| 2-5 | 9.14 | | | |
| Wet, Untreated | | | | |
| A-1 | 8.02 | | | |
| A-2 | 10.58 | | | |

TABLE 2-continued

| Sample # | Stress at Failure (PSI) | Mean UTS (± S.D.) | Mean $V_2$ | Adjusted UTS for collagen (PSI) |
|---|---|---|---|---|
| A-3 | 10.58 | 10.41 ± 2.00 | .251 | 26.2 |
| A-4 | 9.41 | | | |
| A-5 | 13.46 | | | |
| Wet, Treated | | | | |
| B-1 | 12.06 | | | |
| B-2 | 10.45 | | | |
| B-3 | 24.69 | 17.22 ± 6.18 | .273 | 40.9 |
| B-4 | 22.17 | | | |
| B-5 | 16.75 | | | |

While the dry, adjusted UTS shows a 33% decrease after three hours of vapor exposure, the 56% increase in the wet, adjusted UTS is of more significance since the foam is used in the rehydrated state.

EXAMPLE 6

Tests to failure were run to determine the effect of the vapor crosslinking method on the ultimate tensile strength, UTS, of additional collagen-glycosaminoglycan composites.

Six samples of foam #82083A and six samples of foam #82085C were cut to measure 2.5 inches by 2.5 inches. Both foam #82083A and foam #82085C were standard protocol foams which had been processed up to and including the dehydrothermal treatment.

Two samples of each foam were left untreated for use as controls in the tests to failure. The remaining four samples of each foam were vapor crosslinked in either glutaraldehyde or foamaldehyde.

Two glass desiccators were cleaned and placed in a fume hood. In place of desiccant, 60 ml of formaldehyde (37% w/w, balance water and methanol) was poured into one of the desiccators and 60 ml of aqueous glutaraldehyde (25% w/w) was poured into the other. The ceramic grids were then replaced.

Two samples of each foam were placed in each desiccator. The desiccators were covered and left for three hours. At the end of this time, the desiccator tops were slid far enough to one side to allow access for a pair of forceps. All four samples of foam #82083A were removed, two from each desiccator. All four samples of foam #82085C were removed at forty-eight hours of exposure, two from each desiccator.

Tests to failure were run on dry and rehydrated samples for both formaldehyde and glutaraldehyde treated samples. For all tests, a table model Instron with an "A" cell was used. The crosshead speed was two inches per minute and the gage length was one inch.

For all tests, five 0.5-inch by 2.5-inch specimens were cut from each sample of foam. Each specimen was weighed to the nearest milligram. For each pair of samples, five of the specimens were tested dry and five were tested after rehydration.

For the dry tests, the width and length of each specimen was measured to the nearest 32nd of an inch with a ruler. The specimens were then placed in the test fixture and strained to failure. After the test, the thickness of the foam was measured to the nearest 1000th of an inch with a pressure sensitive micrometer (nominal loading of 100 grams).

For the "wet" tests, the samples were rehydrated in 0.05 molar acetic acid for at least five minutes prior to testing. After rehydration, the length and width of the specimen were measured with ruler. The specimens were placed in the test fixture and submerged in 30°–40° C., 0.9% saline solution. This was done to duplicate the conditions in which the foam is used, namely the human body. The specimens were strained to failure, removed, and measured with the pressure sensitive micrometer.

The nominal volume of each specimen was calculated by the product of the three measurements taken with the ruler and the micrometer. The volume fraction, $V_2$, and UTS were calculated as shown in Example 5.

This value was scaled in order to find the UTS for the collagen material itself. This adjusted UTS was found by dividing the results of equation 2 for each specimen by the volume fraction raised to the two-thirds power, as shown in equation 3.

$$\text{Adjusted } UTS_i = UTS_i/(V_2^{\frac{2}{3}}) \quad (3)$$

The mean tensile strengths for all twelve samples are given in Table 3 along with the adjusted UTS for the collagen material. The prefixes C1, F1, and G1 denote foam #82083A used for the control, the three-hour formaldehyde exposure, and the three-hour glutaraldehyde exposure, respectively. The prefixes C2, F2 and G2 denote foam #82085C used for the control, the forty-eight-hour formaldehyde exposure, and the forty-eight-hour glutaraldehyde exposure, respectively.

All stresses listed in Table 3 are in PSI. The means are stated plus and minus one standard deviation. The failure stresses marked with an "*" are from specimens which broke at or in the grips of the test fixture. Stresses so marked were not used in calculating the means.

hyde samples, there is a 63% change over the control for the three-hour treatment versus only a 31% change for the forty-eight-hour treatment.

For the glutaraldehyde samples, there is a 52% change over the control for the three hour treatment versus only a 19% change for the forty-eight-hour treatment.

These changes in strength become much less apparent in the results from the wet tests. Again, the decrease is greater in the samples exposed to formaldehyde than in those treated in glutaraldehyde. Nevertheless, formaldehyde-cross-linked samples still retained adequate strength for clinical use. The results for both the three-hour and forty-eight-hour exposures in glutaraldehyde are well within one standard deviation of the controls. The results of the wet test are more important than the results of the dry test since artificial skins are used in a wet state.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing a crosslinked collagen-glycosaminoglycan composite material, which comprises:
    forming an uncrosslinked composite material from collagen and a glycosaminoglycan; and
    contacting said uncrosslinked composite with a gaseous aldehyde until a crosslinked product having an $M_c$ of from about 800 to about 60,000 is formed.

2. The process of claim 1, wherein said contacting is with air containing vapor from a liquid or solid alde-

TABLE 3

Results of Tests to Failure
Foams #82083A and #82085C, Wet and Dry Tests

| Sample # | DRY | | | | WET | | | |
|---|---|---|---|---|---|---|---|---|
| | Stress at Failure | Mean UTS | $V_2$ | Adjusted UTS | Stress at Failure | Mean UTS | $V_2$ | Adjusted UTS |
| C1-1 | 58.8 | 47.7 ± 8.9 | .047 | 406.6 ± 33.8 | 33.1 | 36.6 ± 11.7 | .160 | 115.5 ± 9.1 |
| C1-2 | 39.7* | | .034 | | 28.7 | | .150 | |
| C1-3 | 38.0 | | .033 | | 57.3 | | .328 | |
| C1-4 | 50.0 | | .044 | | 33.1 | | .150 | |
| C1-5 | 44.1 | | .036 | | 30.9 | | .182 | |
| F1-1 | 19.0 | 16.8 ± 2.3 | .045 | 149.8 ± 2.4 | 13.2* | 19.4 ± 2.5 | .088 | 88.7 ± 12.6 |
| F1-2 | 12.5* | | .033 | | 22.0 | | .141 | |
| F1-3 | 17.6 | | .039 | | 16.2 | | .094 | |
| F1-4 | 13.6 | | .028 | | 19.1 | | .100 | |
| F1-5 | 16.8 | | .038 | | 20.4 | | .084 | |
| G1-1 | 13.0 | 20.8 ± 5.3 | .026 | 193.9 ± 33.5 | 29.4 | 24.6 ± 3.8 | .094 | 111.8 ± 19.9 |
| G1-2 | 24.6* | | .034 | | 20.9 | | .080 | |
| G1-3 | 23.2 | | .033 | | 27.0 | | .117 | |
| G1-4 | 24.6 | | .040 | | 22.8 | | .117 | |
| G1-5 | 22.4 | | .040 | | 27.9 | | .123 | |
| C2-1 | 41.0 | 38.9 ± 9.3 | .034 | 340.2 ± 46.5 | 26.5 | 24.6 ± 3.1 | .100 | 113.6 ± 14.8 |
| C2-2 | 25.7 | | .028 | | 22.0 | | .094 | |
| C2-3 | 47.8 | | .053 | | 27.9 | | .101 | |
| C2-4 | 28.4* | | .037 | | 22.0 | | .109 | |
| C2-5 | 37.0 | | .034 | | 14.7* | | .080 | |
| F2-1 | 28.4 | 28.9 ± 8.7 | .041 | 235.1 ± 32.4 | 17.6 | 18.5 ± 4.9 | .089 | 93.9 ± 14.6 |
| F2-2 | 21.3 | | .031 | | 13.2 | | .059 | |
| F2-3 | 20.0 | | .034 | | 20.6 | | .106 | |
| F2-4 | 40.8 | | .059 | | 15.4 | | .080 | |
| F2-5 | 34.0 | | .047 | | 25.7 | | .100 | |
| G2-1 | 25.7 | 35.2 ± 12.1 | .036 | 275.0 ± 51.4 | 32.0 | 24.8 ± 5.4 | .178 | 100.0 ± 12.0 |
| G2-2 | 34.6 | | .055 | | 17.6* | | .111 | |
| G2-3 | 28.1 | | .032 | | 25.0 | | .111 | |
| G2-4 | 52.5 | | .059 | | 19.1 | | .111 | |
| G2-5 | 19.5* | | .031 | | 23.3 | | .099 | |

The results for the dry tests show a significant decrease in the strength of the collagen/GAG material. This effect is more noticeable in foams treated with formaldehyde than in foams treated with glutaraldehyde. This effect is less noticeable in the longer exposure than in the three hour exposure. For the formaldehyde or from a solution of an aldehyde in water or an organic solvent.

3. The process of claim 1, wherein said contacting is with the vapor of an aldehyde selected from the group consisting of aliphatic mono- and dialdehydes containing up to 8 carbon atoms.

4. The process of claim 3, wherein said aldehyde is formaldehyde, acetaldehyde, glyoxal, or glutaraldehyde.

5. The process of claim 4, wherein said aldehyde is glutaraldehyde.

6. The process of claim 1, wherein said contacting takes place until a crosslinked product having an $M_c$ of from about 8,000 to about 25,000 is formed.

7. The process of claim 1, wherein said uncrosslinked composite material contains less than 1.0% water.

8. The process of claim 7, wherein said uncrosslinked composite material contains less than 0.2% water.

9. The process of claim 8, wherein said contacting is with air containing glutaraldehyde vapor.

10. A crosslinked collagen-glycosaminoglycan composite material prepared by the process of claim 1.

UNITED STATES PATENT AND TRADEMARK OFFICE
CERTIFICATE OF CORRECTION

PATENT NO. : 4,448,718
DATED : May 15, 1984
INVENTOR(S) : Ioannis V. Yannas Et Al It is certified that error appears in the above-identified patent and that said Letters Patent is hereby corrected as shown below:

Column 8, line 50 after Trial #2-Short Term Exposure insert the headings above the three column as follows:

| Exposure time (mins) | Number of Samples | Mean $M_c \pm$ Std Error of the Mean (X $10^3$) |
|---|---|---|

Signed and Sealed this

Twenty-third Day of October 1984

[SEAL]

Attest:

Attesting Officer

GERALD J. MOSSINGHOFF

Commissioner of Patents and Trademarks